Figure 1B:
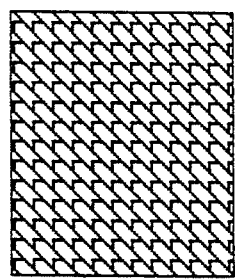

United States Patent [19]
Vijayan

[11] Patent Number: 5,419,758
[45] Date of Patent: May 30, 1995

[54] HEAD BAND FOR MIGRAINE HEADACHE RELIEF

[76] Inventor: Nazhiyath Vijayan, 1215 Vanderbilt Way, Sacramento, Calif. 95825

[21] Appl. No.: 69,532

[22] Filed: Jun. 1, 1993

[51] Int. Cl.$^6$ .......................... A61H 7/00; A61F 5/08
[52] U.S. Cl. ........................................ 602/74; 606/204
[58] Field of Search ............... 602/17, 60, 61, 74, 602/75; 128/857; 2/171.2, DIG. 7, DIG. 11; 606/204, 204.15

[56] References Cited

U.S. PATENT DOCUMENTS

| | | |
|---|---|---|
| 763,814 | 6/1904 | Turner . |
| 841,714 | 1/1907 | Peters . |
| 854,509 | 5/1907 | Mabey ................................ 602/74 |
| 937,596 | 10/1909 | Gray et al. . |
| 1,250,273 | 12/1917 | Brady ................................ 602/74 |
| 1,324,975 | 12/1919 | Morris ................................ 602/74 |
| 1,481,354 | 1/1924 | Dinofeld ............................. 602/74 |
| 2,571,461 | 10/1951 | Livingston et al. ............. 602/17 X |
| 4,632,104 | 12/1986 | Conrow . |
| 4,665,909 | 5/1987 | Trainor ............................ 602/75 X |
| 4,944,269 | 7/1990 | Matthews ........................... 606/204 |
| 5,120,300 | 6/1992 | Shaw ................................. 602/61 |

*Primary Examiner*—Richard J. Apley
*Assistant Examiner*—Beverly A. Meindl

[57] ABSTRACT

A smooth but strong elastic band (1) with a Velcro attachment at one end (2) so that it can be applied tightly around the head to compress dilated blood vessels in order to provide relief of migraine headache pain. Additional firm rubber disks (3) are inserted between the band and the scalp to direct more localized pressure over areas with more severe pain.

1 Claim, 1 Drawing Sheet

HEAD BAND FOR MIGRAINE HEADACHE RELIEF

BACKGROUND—FIELD OF INVENTION

This invention relates to the development of a head band specifically to apply continuous and comfortable pressure to the scalp to relieve migraine headache pain.

BACKGROUND OF INVENTION

Migraine headache is a very common disorder. This leads to disabling and intermittent episodes of head pain in many of its sufferers. Present day scientific knowledge has concluded that the major part of the pain arises from dilatation and stretching of blood vessels in the scalp. There are specific medications in the market to treat this type of headache. These drugs act by constricting the dilated blood vessels. These are not always helpful and often cause side effects. Many patients therefore resort to non-drug type of treatments.

Migraine sufferers often seek relief by applying finger pressure over the areas of most severe pain. A migraine may last for hours to days. Therefore it is not possible to sustain this type of pressure over a long period of time without one's fingers becoming fatigued. Some individuals tie pieces of clothing around the head to apply pressure. This is not very practical because it is not possible to apply uniform and adequate amount of pressure all around the head. Besides, when such a piece of clothing is applied, it will not be possible to administer more localized pressure over areas of most severe pain. Recent studies have concluded that providing both generalized and localized pressure at the same time leads to a better control of headache pain.

BACKGROUND—DESCRIPTION OF PRIOR ART

Various devices have been developed over the years in order to help this problem. Four such devices have been patented in the past. U.S. Pat. No. 763,814 to Turner (1904) describes an appliance with a piece of metal placed across the crown of the head. This does not provide any generalized pressure. There are 2 pieces of wood attached to the ends of the metal part which deliver pressure over the temples. However there is no mechanism for adjusting the amount of pressure applied. The entire device is cumbersome and does not provide local or general pressure adequately.

U.S. Pat. No. 841,714 issued to Peters (1907) describes a "head-truss". This consists of 2 metal pieces set at 90 degrees with pads attached at the ends of each member and one pad at the crossing point of the two members on top of the head. This basically has the same design as Turner's except for the additional pads. This can apply pressure only in a local fashion. There are no provisions for adjusting the amount of pressure applied.

U.S. Pat. No. 937,596 issued to Gray and Hitchcock (1909) is also similar in its approach and uses metal parts with pads with no adequate provision for applying pressure where it is needed and also in the amount needed.

U.S. Pat. No. 4,632,104 issued to Conrow (1986) is more complex. The theory behind its supposed effectiveness is physically moving part of the skull bone to alter the blood flow. This is not possible from a practical point of view. The device requires insertion of ear ;pieces which are connected to a headband. Tension is applied in order to pull the ears forward. This is extremely cumbersome and certainly will be very uncomfortable to wear for any length of time. Besides, there are no means of applying direct pressure over the blood vessels or over other areas of scalp where there is pain.

In conclusion, all these earlier devices suffer from number of shortcomings. These include the cumbersome nature of the whole apparatus, lack of adequate provision for application of sufficient pressure where it is most needed and the obvious discomfort of using metallic contraptions on one's head for long periods of time.

OBJECTS AND ADVANTAGES

The present invention was designed to overcome the disadvantages of the previous devices. These advantages include:

(a) the elastic band applied around the head provides a uniform pressure all around the head;
(b) the amount of pressure applied can be easily adjusted by stretching or relaxing the elastic band as needed;
(c) the elastic band is made out of soft but strong material so that it is very comfortable to the user;
(d) firm but pliable disks are applied between the band and the scalp to provide more concentrated pressure over areas of maximum pain;
(e) the amount of pressure at any location can be adjusted by stacking the disks one on top of each other;
(f) these disks can be applied at any number of locations; and
(g) it has a very simple design which can be constructed from very easily available materials.

In conclusion, this band provides a very simple, easy to use and comfortable device. At the same time it is capable of providing adequate and appropriate amount of pressure over the dilated scalp blood vessels in order to relieve migraine headache pain.

DRAWING FIGURES

Figure 1A:
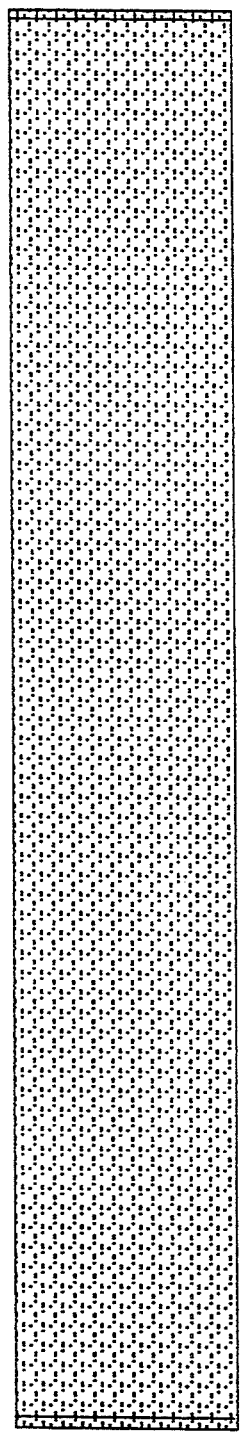
Figure 1C:
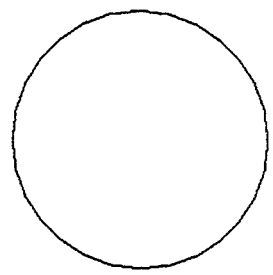

FIG. 1a shows the elastic band. FIG. 1b shows that Velcro attachment positioned at one end of the band for fastening the band around the user's head. FIG. 1c shows a firm rubber disk for insertion between the elastic band and the user's scalp.

REFERENCE NUMERALS IN DRAWING 1 elastic part of the band
2 Velcro hooks at the end of the elastic band
3 rubber disk

DESCRIPTION—FIGURE

The band has a wide and long elastic part (1) which can be made of any strong elastic material which is soft. A small piece of Velcro (2) is attached to one end of the band so that it can be fastened to the main part of the band. The dimensions of parts 1 and 2 are sufficient to accommodate the degree of individual variations of the head size. Part 3 is a small circular firm rubber disk. The size and thickness of this part can also be varied depending on the requirements.

OPERATION

This device is very easy to use. When headache pain appears, the person will simply apply the band around the head and attach it with the Velcro. The amount of pressure can be easily varied depending on how much stretching is applied. The pressure used should be within the comfort zone which can be determined by the individual. At the same it should be tight enough to apply sufficient pressure to compress the dilated blood vessels. The person then determines the areas on the scalp where there is more severe pain which cannot be controlled by the band alone. Rubber disk(s) are inserted over these locations, under the band. The degree of pressure applied can be adjusted by stacking more than one disk in the same location, if needed. Excess pressure which causes discomfort should be avoided. The device has been found to be very effective in actual use.

SUMMARY, RAMIFICATIONS AND SCOPE

Accordingly, the reader can see that this is a very simple but very effective means of applying pressure to the dilated blood vessels of the scalp during migraine headache to control pain. It has additional advantages in that:

- it is very easy to apply to the scalp;
- the amount of general or local pressure can be easily adjusted;
- it can be worn for long periods of time without any discomfort; and
- it can be manufactured very easily from readily available materials.

Although the description above contains many specifications, these should not be construed as limiting the scope of the invention but as merely providing illustrations of some of the presently preferred embodiments of this invention. For example, the band can have other sizes and shapes, the disks can be of different materials, disks can be cooled before use in order to provide additional relief and the method of attaching the band to the scalp can be varied.

Thus the scope of the invention should be determined by the appended claims and their legal equivalents, rather than by the examples given.

I claim:

1. A method of relieving headache pain comprising the steps of:
    a) providing an adjustable elastic band having predetermined size and shape and first and second ends, hook and loop fasteners located at said first and said second ends, respectively, wherein said band is adapted to encircle the head to apply varying degrees of pressure uniformly and continuously around the scalp;
    b) providing firm disks insertable between said band and the scalp to apply more effective localized pressure over areas of maximum pain;
    c) applying said band around the head and attaching said hook and loop fasteners;
    d) inserting said firm disks at user determined locations around the circumference of the head;
    e) determining areas of severe pain; and
    f) inserting additional firm disks at areas of severe pain such that additional firm disks are stacked one on top of another.

* * * * *